(12) United States Patent
Esmaeili

(10) Patent No.: US 6,816,244 B2
(45) Date of Patent: Nov. 9, 2004

(54) DETERMINING OPTICAL FIBER TYPES

(75) Inventor: Sasan Esmaeili, Solna (SE)

(73) Assignee: Telefonaktiebolaget LM Ericsson (publ), Stockholm (SE)

( * ) Notice: Subject to any disclaimer, the term of this patent is extended or adjusted under 35 U.S.C. 154(b) by 0 days.

(21) Appl. No.: 10/311,849

(22) PCT Filed: Jun. 20, 2001

(86) PCT No.: PCT/SE01/01427
§ 371 (c)(1),
(2), (4) Date: Apr. 15, 2003

(87) PCT Pub. No.: WO01/98799
PCT Pub. Date: Dec. 27, 2001

(65) Prior Publication Data
US 2003/0164939 A1 Sep. 4, 2003

(30) Foreign Application Priority Data
Jun. 20, 2000 (SE) ................................. 0002310

(51) Int. Cl.[7] .............................................. G01N 21/00
(52) U.S. Cl. ..................................................... 356/73.1
(58) Field of Search ..................... 356/73.1; 385/88–90, 385/95–99, 147; 219/121.11, 121.45, 57; 65/407, 152, 501; 374/160, 188

(56) References Cited
U.S. PATENT DOCUMENTS

| 4,027,977 | A | | 6/1977 | Frazee, Jr. et al. |
| 4,882,497 | A | | 11/1989 | Inoue et al. |
| 5,176,731 | A | | 1/1993 | Prast et al. |
| 5,365,329 | A | | 11/1994 | Svendsen |
| 5,638,476 | A | * | 6/1997 | Zheng ........................ 385/96 |
| 5,909,527 | A | * | 6/1999 | Zheng ........................ 385/96 |
| 5,961,865 | A | | 10/1999 | Esmaeili et al. |
| 6,046,798 | A | | 4/2000 | Zamzow |
| 6,499,319 | B1 | * | 12/2002 | Esmaeili ...................... 65/484 |

FOREIGN PATENT DOCUMENTS

| EP | 0864889 A2 | 9/1998 |
| SE | 9002725-1 | 8/1990 |
| SE | 9100979-5 | 4/1991 |
| SE | 9201817-5 | 6/1992 |
| WO | 9612980 A1 | 5/1996 |

OTHER PUBLICATIONS

A Splicing and Inspection Technique for Single Mode Fibers using Direct Core Monitoring, Kawata et al., Journal of LIghtwave Technology, vol. Lt–2, No. 2, Apr. 1984.

* cited by examiner

Primary Examiner—Tu T. Nguyen
(74) Attorney, Agent, or Firm—Nixon & Vanderhye P.C.

(57) ABSTRACT

To determine the type of unknown optical fiber, an automatic fiber fusion-type splicer is used having movable clamps, electrodes, camera devices and background illumination, coupled to electronic circuits containing control, driver, and interface circuits. A fiber portion is imaged to allow the fiber core to be distinguished in the captured image, both when the fiber is cold and when it is heated. From a first fiber picture in a heated state, a first light intensity profile is determined along a line perpendicular to the fiber. The profile derivative is compared to derivatives of known light intensity profiles. Similar procedures are performed for the cold fiber. Based on the comparing operations, the type of the tested fiber is determined.

14 Claims, 14 Drawing Sheets

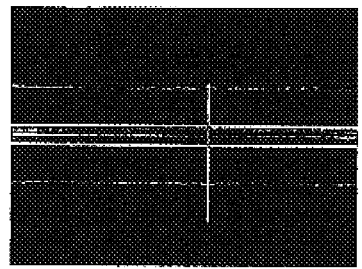
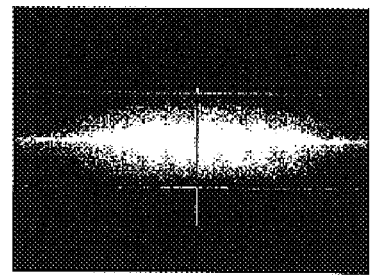
Fig. 8a　　　　Fig. 8b
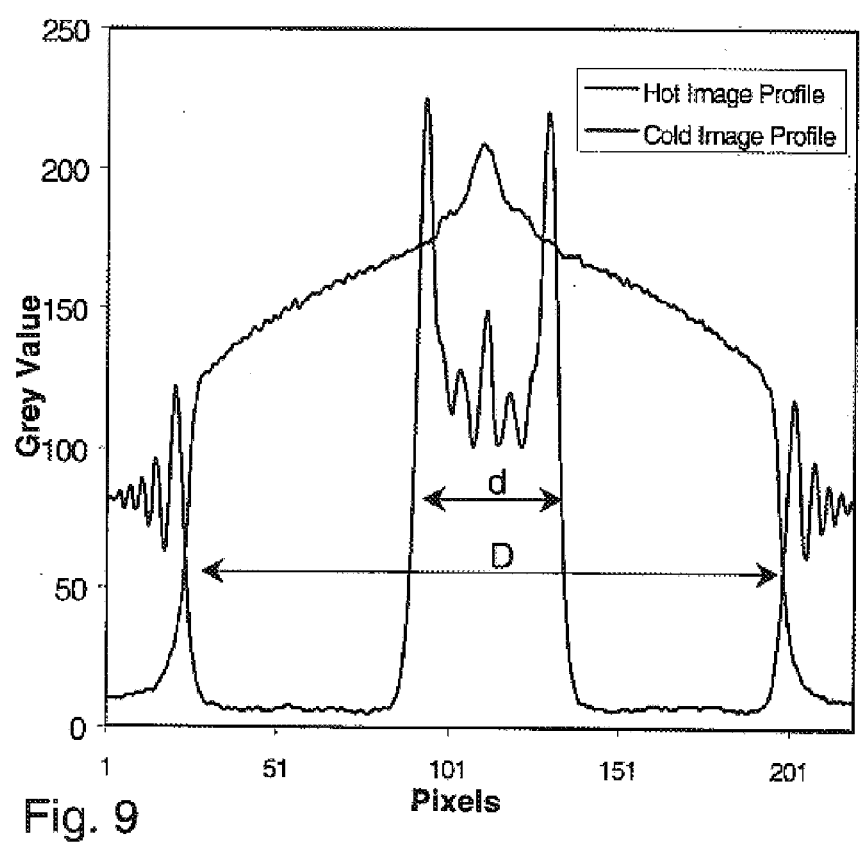
Fig. 9

DETERMINING OPTICAL FIBER TYPES

This application is the US national phase of international application PCT/SE01/01427, filed in English on Jun. 20, 2001, which designated the U.S. PCT/SE01/01427 claims priority from SE application 0002310-1, filed on Jun. 20, 2000.

TECHNICAL FIELD

The present invention relates to a method for evaluating an optical fiber, in particular for determining the general type of optical fiber to which a considered optical fibers belongs, to be used in an automatic fiber splicer for automatically selecting correct splicing parameters and also to a method of setting an optical system used in a splicer.

BACKGROUND

Equipment and methods for aligning and splicing silica based optical fibers has been developed and improved for many years. The most common method for performing an alignment of optical fibers to be spliced with an accuracy better than 0.2 micron and making accurate splice loss estimation has comprised advanced digital image processing of magnified pictures of the splicing position before, at and after the actual splicing of the fibers, these pictures produced by a camera system. The design of a compact optical system, capable of giving a sharp image of the spliced fibers and their cores before, during and after the splicing which in many cases is made by a fusion process, has been a critical task in developing fiber splicing machines having a high performance, see e.g. T. Haibara, M. Matsumoto, T. Tanifuji and M. Tokuda, "Monitoring method for axis alignment of single-mode fiber and splice loss estimation", Optics Letters, Vol 6, No. 4, April 1983, O. Kawata, K. Hoshino, Y. Miyajima, M. Ohnishi and K. Ishihara, "A splicing and inspection technique for single-mode fibers using direct core monitoring", J. Ligthwave Technology, Vol. LT-2, No. 2, April 1984, and T. Katagiri, M. Tachikura and I. Sankawa. "Optical microscope observation method of a single mode optical fiber core for precise core-axis alignment", J. Ligthwave Technology, Vol. LT-2, No. 3, June 1984.

In a fusion splicer equipped with a digital camera system, the fibers to be spliced or being spliced or having been spliced are conventionally illuminated by a light source, normally a LED, located at a distance behind the fibers as seen from a lens system. The lens system is focused on some point in the fiber claddings or in the fiber cores and a magnified image of the fibers is created on a CCD matrix (Charge Coupled Device). The electric signal from the camera is A/D converted, and the digital picture is processed in a computer system. The measurement data from the pictures are then used for moving fibers to the desired accurate alignment and for estimating the splice loss.

The optical system of a fusion splicer can also be adapted to image the hot fibers during fusion, see e.g. German patent 40 04 909 and Swedish patent application 9002725-1, filed Aug. 24, 1990. The small difference between emissivity of the fiber cladding and the core at high temperatures, such as those of about 2000° C. existing in an electric arc used in the fusion process, make it possible to produce a bright image of the core, conventionally located in the middle of the fiber. The visible and near infrared part of the emitted waves from the heated fibers are collected and detected by the camera system. Hot images can be used for real time processing of the fibers during fusion and for making an accurate splice loss estimation after the splice is completed.

It is well known that core/cladding eccentricity, cleave angle, curl, fiber-end contamination and mode field diameter (MFD) mismatch are the main reasons of fusion splicing loss. An MFD mismatch can significantly influence the splice loss in particular in the case where different types of fibers are spliced to each other. To produce splices having a low loss made between fibers having different MFD it is necessary to characterize the types of fibers to be splice and based on the fiber types, select appropriate splice parameters like overlap, fusion heat and fusion time to be used in the splicing procedure, see e.g. W. Zheng, "Real time control of arc fusion for optical fiber splicing", J. Ligthwave Technology, Vol. 11, pp. 548–553, March 1994, and W. Zheng, O. Hultén and Robert Rylander, "Erbium doped fiber splicing and splice loss estimation", J. Ligthwave Technology, Vol. 12, pp. 430–435, March 1994. The appropriate choice of these parameters is highly dependent on the core sizes and the refractive index profiles of the fibers and the refractive index differences between the core and cladding. A method for identifying fibers before fusion for automatic selection of the splice parameters is therefore of great importance for making low loss splices of different types of fibers.

In Swedish patent application 9100979-5 for Telefonaktiebolaget L M Ericsson, inventors Ola Hultén and Wenxin Zheng, a method of determining characteristics of optical fibers is disclosed, the method including analyzing images of heated fibers and in particular light intensity profiles along lines perpendicular to the fibers. The general shape of the central peak and especially its width and height are evaluated. A mathematical method using the same basic analyzing process is disclosed in Swedish patent application 9201817-5 for Telefonaktiebolaget L M Ericsson, inventor Wenxin Zheng.

In an automatic fiber splicer the optical system for imaging an optical fiber on some light sensitive area cannot be easily set for different imaging conditions such a for producing a sharp picture of a cold fiber in which the core is visible or in particular the position and the width of the core are detectable or for producing a sharp picture of a heated optical fiber emitting light so that also in this picture the core region is detectable. Such focusing for different imaging conditions is generally made manually by observing the captured images for different focusing conditions, i.e. for different distances between the object, the optical fiber, and the imaging system, primarily the lens system.

SUMMARY

It is an object of the invention to provide a reliable method of deciding the type of an optical fiber.

It is another object of the invention to provide a robust, automatic method of setting an optical system for providing images of an optical fiber in which the core of the optical fiber is visible.

In determining the kind or type to which an unknown optical fiber belongs an automatic fiber splicer using fusion-welding is used having movable clamps or retainers for positioning aligning two fibers, electrodes for producing when energized an electric arc, camera devices such as CCD-matrices and light sources producing a background illumination. These devices are all coupled to electronic circuits containing control means (33) and the necessary driver and interface circuits. A portion of the fiber held one of the clamps is imaged on the light sensitive areas of the cameras through high-resolving lens systems, allowing the core of the fiber to be distinguished in the captured image, both when the fiber is cold and when it is heated such as to about or somewhat lower temperatures used in fusion-splicing and then issue sufficient light for capturing images without using any background illumination. From a first picture taken of the fiber in a heated state a first light intensity profile along a line substantially perpendicular to the longitudinal direction of the fiber is determined in an image processing and analysis module. This profile is further analyzed by calculating the derivative of the profile and comparing the derivative to derivatives of light intensity profiles previously determined for a optical fibers of known different kinds or types. A second picture is taken of the cold fiber for which a second light intensity profile can be similarly determined. This profile is then compared to corresponding profiles previously determined for the known optical fibers. The results of the comparing operations are finally evaluated to decide the kind of the tested fiber.

In an automatic fiber splicer a correct automatic focusing for different imaging conditions can be obtained by executing the following steps in a successive order. The distance between the optical fiber and the optical system of the splicer is varied and pictures are taken for different distances. In the pictures taken light intensity profiles are determined as above which are analyzed to find a measure of the apparent diameter of the optical fiber and a measure of the apparent width of the central peak which is normally obtained in such profiles and corresponds to the high intensity region in the center of the fiber and which at least for a high-resolving optical system corresponds to the core of the fiber. The ratio or quotient of these two measures is calculated and compared to a predetermined value. The distance giving a picture in which the ratio of the measure values agrees with the predetermined value or at least deviates as little as possible from that value is taken as the distance giving a correct imaging. It turns out that by measuring on fibers of different types a predetermined value can be determined which produces good pictures of cold pictures from which valuable information of the core such as its diameter can be obtained and a different predetermined value can be determined producing correspondingly good pictures of heated fibers.

Additional objects and advantages of the invention will be set forth in the description which follows, and in part will be obvious from the description, or may be learned by practice of the invention. The objects and advantages of the invention may be realized and obtained by means of the methods, processes, instrumentalities and combinations particularly pointed out in the appended claims.

BRIEF DESCRIPTION OF THE DRAWINGS

While the novel features of the invention are set forth with particularly in the appended claims, a complete understanding of the invention, both as to organization and content, and of the above and other features thereof may be gained from and the invention will be better appreciated from a consideration of the following detailed description of non-limiting embodiments presented hereinbelow with reference to the accompanying drawings, in which:

FIGS. 8a and 8b are cold and hot images of a typical dispersion shifted fiber imaged by the lens system of FIG. 6 as captured by a CCD-camera, the cold image taken when the fiber is laterally illuminated by a red LED ($\lambda_c$=660 nm) and the hot image taken during fusion, when temperature of the fiber is approximately 1900° C., FIG. 9 is a plot of hot and cold image profiles of the dispersion shifted fiber of FIGS. 10a, 10b in grey scale values.

DETAILED DESCRIPTION

Figure 1A:
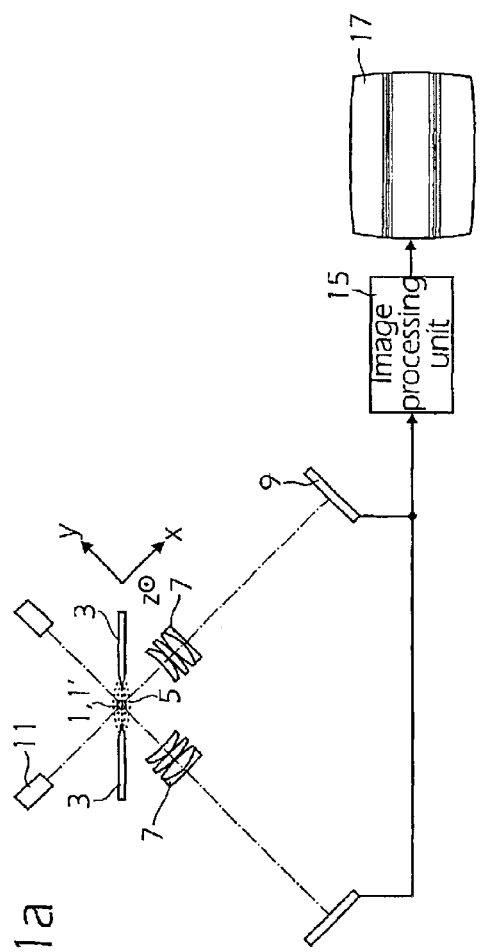
FIG. 1a is a schematic picture of a setup for fusion-splicing two optical fibers to each other.

In FIG. 1a the basic setup in an automatic optical fiber splicer is shown which is similar to that used in a prior art ribbon fiber splicer, see U.S. Pat. No. 5,961,865. The optical fibers 1, 1' to be or being spliced have their end regions located between points of electrodes 3, between which an electrical discharge 5 is generated for heating the fiber ends, the intensity of the electrical discharge being controlled by the intensity of the electrical current between the electrodes 3. Optical lens systems 7 depicts, in two perpendicular directions, the fiber end regions on light sensitive areas 9, typically plates carrying a matrix of CCD elements. The splice position can be illuminated by suitably placed light sources such as LEDs 11 providing a background illumination when required. A digital imaging processing system 15 processes the electric signals from the light sensitive areas 9 to monitor the fibers used and the splicing procedure by controlling fiber positioning devices and the intensity of the electrode current. The image processing system is connected to a monitor or display element 17 for showing the captured images.

Figure 1B:
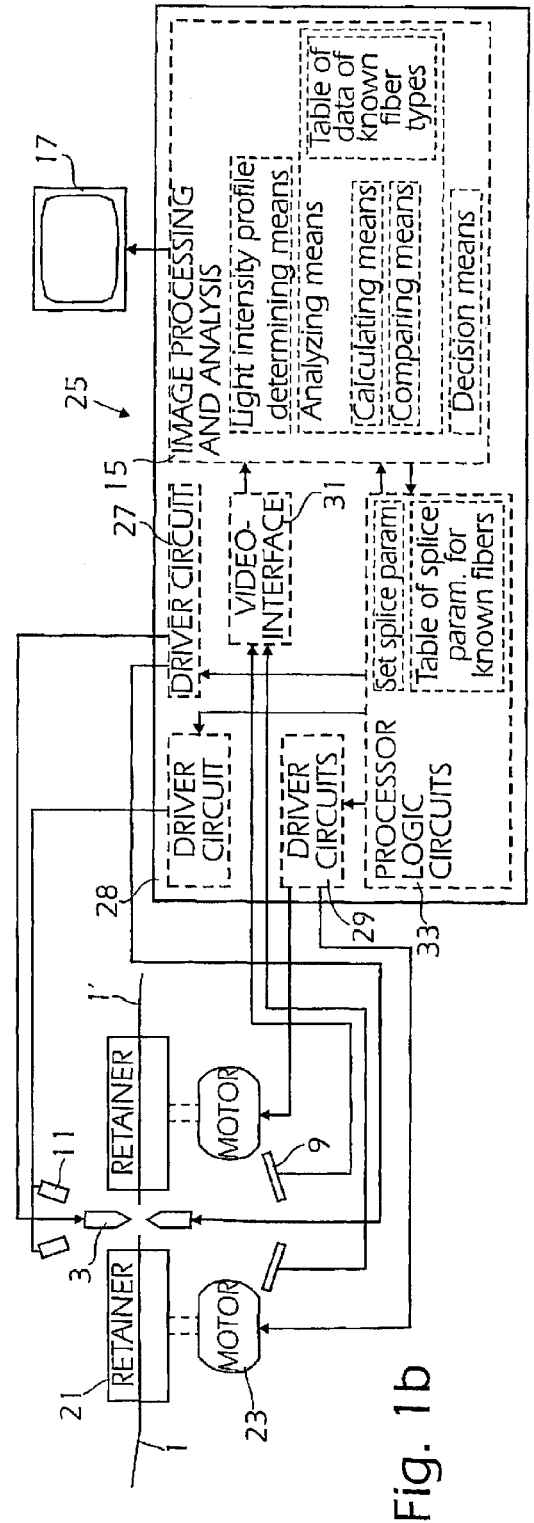
FIG. 1b is a schematic picture similar to that of FIG. 1a also showing some components of electronic control circuits.

In the schematic picture of FIG. 1*b* some more electrical details of a fiber splicing device of the automatic type are shown. Thus, the splicing device has fixtures or retainers 21, in which the end portions of the fibers 1, 1' are placed and firmly held during the positioning and the splicing. The retainers are movable in three orthogonal coordinate directions both in parallel to the longitudinal direction of the fibers and in two directions perpendicular to this direction. The retainers 21 are thus displaced along suitable mechanical guides, not shown, by control motors 23. Electric lines to the electrodes 3, the light sources 11 and the motors 23 extend from an electronic circuit module 25, from driver circuits 27, 28 and 29 respectively of the circuit module. From the light sensitive areas 9 electric lines are arranged to a video interface 31 in the electronic circuit module 25, from which a suitable image signal is delivered to the image processing and image analysis unit 15. The various procedural steps are controlled by a control circuit 33 of the circuit module, e.g. a suitable micro processor. The control circuit 33 performs the procedural steps mentioned above and thus controls the displacement of the fiber ends in relation to each other by energizing the motors 23 in suitable displacement directions, provides electrical current to the light sources 11 when pictures e.g. for the alignment procedure have to be captured, and provides a signal to the image processing and image analysis unit 15 for starting an analysis of an obtained image. Further, the control circuit 33 controls the time, when a fusion current is to be started to be provided to the electrodes 5 and the time period during which this current is to be delivered and the intensity of the fusion current.

Figure 2A:
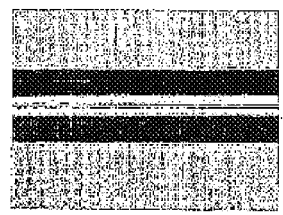
FIG. 2a is a cold image of an optical fiber, when the fiber is laterally illuminated by a light source.
Figure 2B:
FIG. 2b is a hot image of an optical fiber, captured in a fusion process when the fiber glows and radiates light.

In order to obtain images of cold fibers in which the fiber cores are visible and which are suited for digital processing, the lens systems 7 used must have special performance characteristics and features. Thus, the lens systems 7 must be capable of imaging the cores of the optical fibers both when the fibers are not heated and are laterally or from behind illuminated by a separate light source to get a "cold image" and such a picture is seen in FIG. 2*a* of a typical single-mode fiber. The lens systems 7 must also be capable of imaging the fibers during the fusion process when the fibers are hot and emit thermal radiation to get a "hot image", see the picture of FIG. 2*b* of the same fiber as in FIG. 2*a*.

Figure 3:
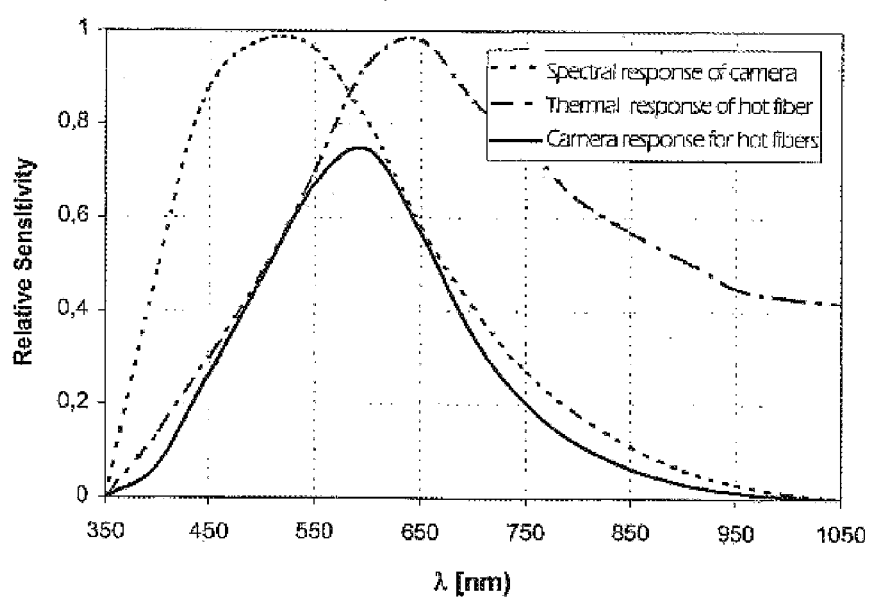
FIG. 3 is a diagram showing the radiation spectrum of an optical fiber in fusion, the spectral response of a CCD-camera and the product of the radiation spectrum and the spectral response.

The imaging system of a fiber splicer also contains the CCD matrices or CCD-cameras 9 which must be capable of capturing ordinary pictures and also detecting the radiation emitted by the hot fibers. FIG. 3 is a diagram showing the measured radiation spectrum from a hot fiber having a temperature of approximately 1900° C. The spectral response of the CCD-camera and its product by the hot-fiber radiation are also plotted in the diagram, the latter plotted curve demonstrating that the CCD-camera is sufficiently sensitive to the light emitted by hot fibers. Thus, achromatic lens systems 7 can create sharp "hot images" as captured by the CCD-devices 9.

Figure 4:
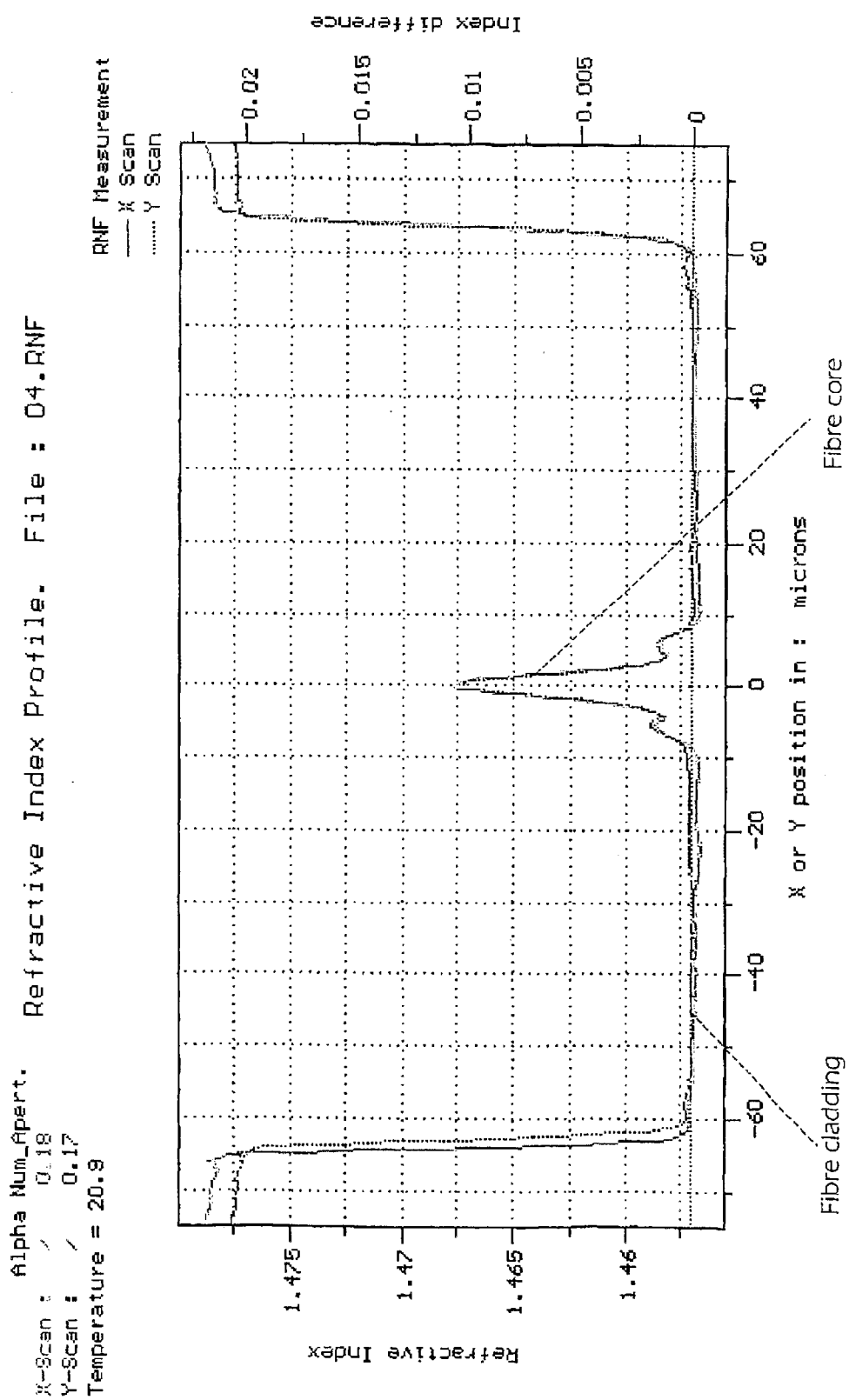
FIG. 4 is a diagram of the refractive index profile of a dispersion shifted fiber measured by a fiber geometry scanner.
Figure 5:
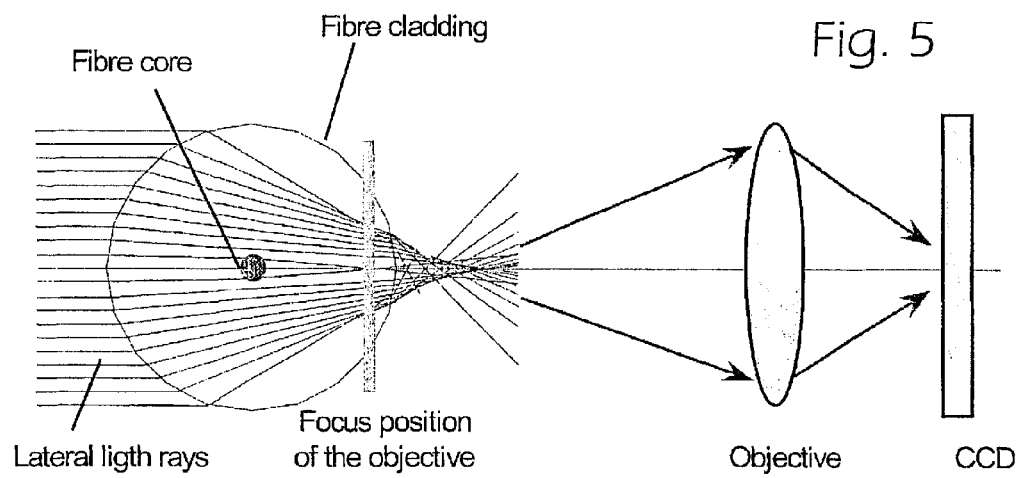
FIG. 5 is a schematic view illustrating refraction of collimated lateral rays from a light source by an optical fiber.

FIG. 4 is diagram showing a plot of the refractive index profile of a dispersion-shifted optical fiber as measured by a near-field fiber geometry scanner. The diameter of the fiber was 125 $\mu$m and the core diameter was approximately 4 $\mu$m. The index difference between core and cladding can in the diagram be read to comprise almost 0.01. This slightly higher index of the core is large enough to make the core behave as a thin cylindrical lens placed inside the fiber, the core refracting the lateral light rays from a light source placed at some distance behind the fiber as seen in FIG. 5. A camera system including a high numerical aperture objective, focused approximately at the focal point or more correctly at a point on the focal line of the fiber core, will thus be capable of producing a picture of the core, see the articles cited above.

A summary of the data for a lens system suited to produce good cold images and good hot images is given in Table 1.

TABLE 1

| Item | Target Cold Image | Target Hot Image |
|---|---|---|
| Optical Magnification | >8x | >8x |
| Conjugate Length | <125 mm | <125 mm |
| Object distance | >11.0 mm | >11.0 mm |
| Field of view | 0.25 mm | 0.25 mm |
| Numerical Aperture | >0.38 | — |
| Resolution Power (MTF) on axis | >40% at 400 c/mm | >50% at 100 c/mm |
| Spectral Bandwidth | 610–690 nm | 500–700 nm |
| Distortion | <0.01% | <0.01% |

Figure 6:
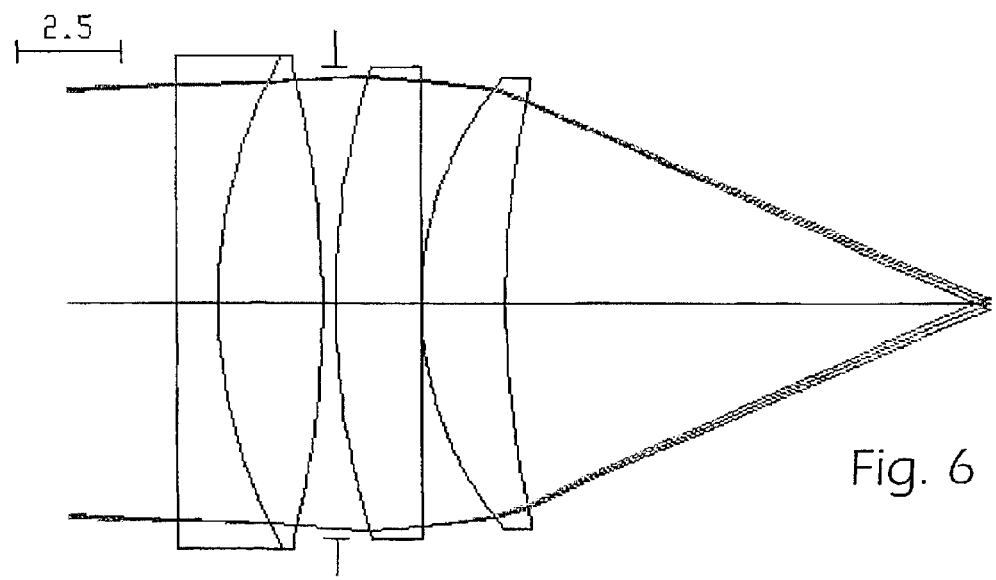
FIG. 6 is schematic sectional view showing the design of a high-resolving lens system.

A lens according to Table 1 having a low number of lens elements, in which the effect produced by production variation of dimensions was minimized, was chosen to have a basic configuration analogous of a retrofocus camera lens, see FIG. 6. The objective was made of two positive components and a negative doublet placed in the long conjugate. The conjugate length was 121 mm for an object distance of 11.1 mm.

Figure 7A:
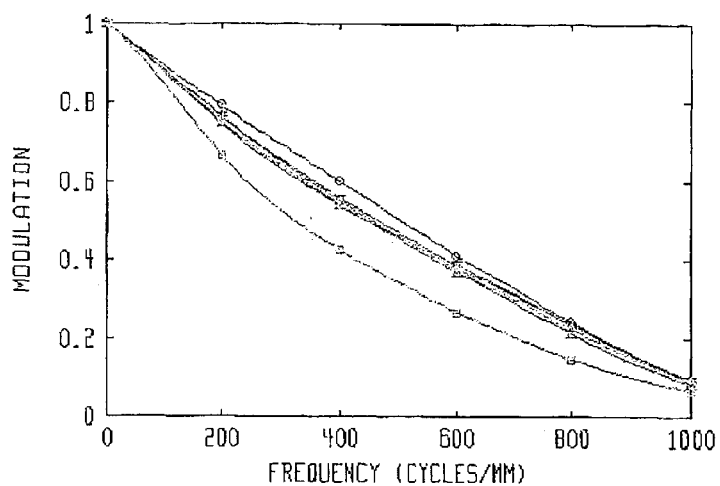
FIG. 7a is a plot of the modulation transfer function of the lens system of FIG. 6 for three wavelengths in the range of 610–690 nm, also showing the ideal MTF (diffraction limited)
Figure 7B:
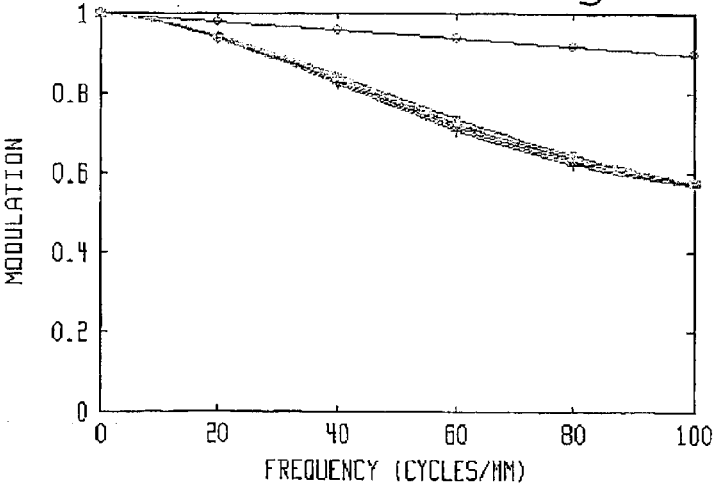
FIG. 7b is a plot similar to that of FIG. 7a for wavelengths in the range of 500–700 nm.

FIGS. 7*a* and 7*b* show plots of the Modulation Transfer Function for the selected lens system for two spectral intervals. Thus, FIG. 7*a* illustrates the resolution power of the objective for "cold images" using a background illumination from a 610–690 nm light source and FIG. 7*b* for "hot images", i.e. for thermal radiation from glowing fibers detected by the CCD-camera, in the wavelength range of 500–700 nm.

An automatic fusion splicer having an imaging system capable of capturing both cold and hot images can be used for making a reliable determination of the kind of optical fibers to be spliced as will be demonstrated hereinafter. Thereby, correct parameters to be used in the splicing process can be selected to give splices having improved properties such as low insertion losses. A process for such identification will now be described.

Thus, FIGS. 8*a*, 8*b* show cold and hot images respectively of a typical dispersion shifted fiber taken by the lens system as described above. The core is sharply visible in the hot image due to the higher emissivity of the doped core glass. The intensity (gray level) profiles of the cold and hot images are given in FIG. 9 as functions of the pixel position in the captured images, the pixel positions corresponding to a physical position in fiber taken along the solid lines, drawn on the pictures, extending perpendicularly to the longitudinal direction of the fiber. The center of the fiber core is visible as a central peak and the thin ring around the core can be seen as two lower peaks at each side of the core in the cold image profile. The fiber core can also be seen as the central peak of the hot image profile. The image of the ring is partly superimposed on the picture of the core and can be observed as increased gray-level values around the core in the hot image profile.

The cold image profile and the hot image profile contain information on the geometry and the shape of the fiber core. This information can be further processed to identify the kind of optical fiber used. Such a process will now be described with reference to the flow diagram in FIG. 12.

In a first block 81 the focus position of the camera is set to a first value $t_1$ given by $$t_1 = \frac{d_c}{D} = 0.24 \qquad (1)$$

where D is the diameter of the fiber as seen in the cold image and $d_c$ is width of the refracted illumination rays at half the maximum in the cold image as shown in FIGS. 5 and 9. This means that in the focusing step pictures are taken when varying the focus position of the lens system 7 and then analyzed to determine the values $d_c$ and D, until, in a captured image, the relation (1) is valid, i.e. so that the ratio of the half-width value $d_c$ to the apparent diameter D is equal to a predetermined value. This digital cold-image having the desired ratio is then stored in a memory of the process circuits 33. Then in a block 83 the focus position of the camera is changed to $t_2$ $$t_2 = \frac{d_h}{D} = 0.48 \qquad (2)$$

where $d_h$ in the corresponding manner is the width of the refracted illumination rays at half the maximum in the hot image. Thus, in this case the same procedure is executed but now there is no background illumination, i.e. the light sources 11 are not energized, but the arc between the electrodes 9 is lit by providing a suitable current to flow through the electrodes. The electrode current should be lower than that used for actually fusing the ends of the fibers to each other. The focus position is varied, pictures are captured and analyzed to find the half-width value $d_h$ and the apparent diameter D, until the focus position gives a picture in which the condition (2) is fulfilled, i.e. in which the ratio of said quantities is equal to a predetermined value larger than that used for setting the focus position for cold images, e.g. equal to about twice that value Then this digital hot-image is stored in the processor memory.

A 3×3 mean filter is in the next block 85 applied to the gray-level values of the whole or some selected area of the stored hot image taken for the correct focus position. In the block 87 the hot fiber profile $F_h(x)$ which is a function or more exactly a one-dimensional array containing gray-level values of the picture of points on a line perpendicular to the longitudinal direction of the hot image of the fiber, is selected from the filtered area, this line thus extending in the x-coordinate direction and x representing the position in this direction. The values $F_h(x)$ are thus measured values representing the intensity of light emitted from the corresponding points of the fiber. A differential array, $G_h(x)$ with accentuated spatial amplitude changes is then generated in the same block and is given by Eq. (3).

$$G(x) = F(x+1) - F(x-1) \qquad (3)$$

In the same block 87 also the cold fiber profile $F_c(x)$ is selected which in the corresponding way is a one-dimensional array containing gray level values of the picture of points on a line perpendicular to the longitudinal direction of the fiber. The values $F_h(x)$ are thus measured values representing the intensity of light coming from the cold fiber.

Figure 10:
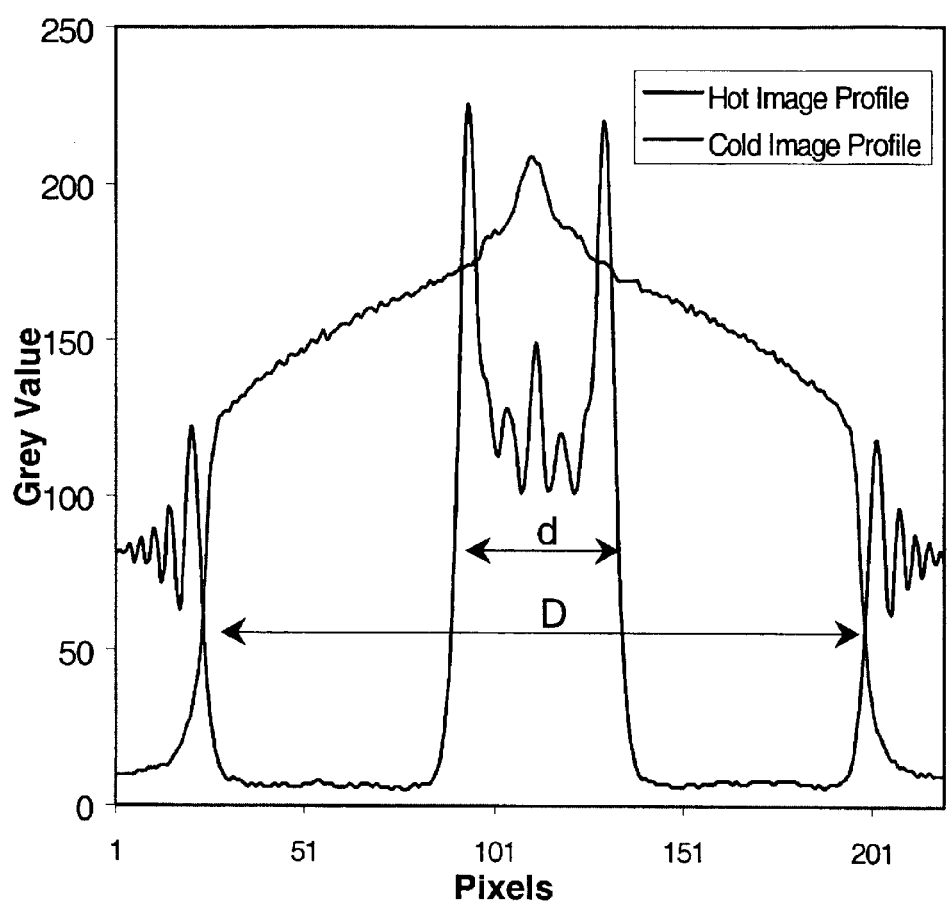
FIG. 10 is a plot of the hot image profile F(x) and its first order derivative G(x) for the dispersion shifted fiber of FIGS. 8a, 8b.
Figure 11:
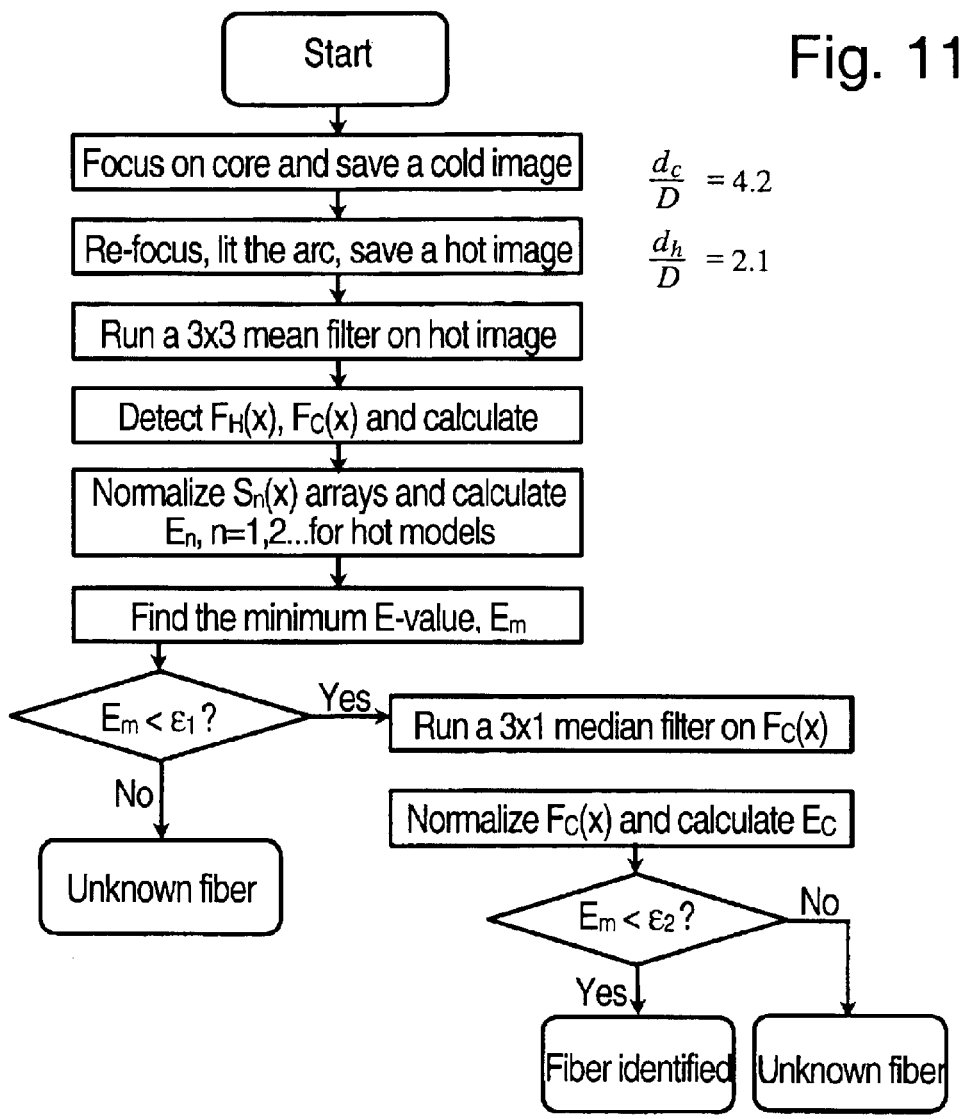
FIG. 11 is flow diagram illustrating a procedure for fiber identification.

The hot grey-level array or hot fiber profile $F_h(x)$ for the dispersion shifted fiber for which the images in FIGS. 8a, 8b are taken is plotted in FIG. 10 and in the same figure its first order derivative $G_h(x)$ containing 225 pixels is also plotted. Boundaries of the core and the ring are clearly detected as four local maximum points at the middle of the curve of the derivative. They can be compared to the four local minimum points at the middle of the cold-image profile, see FIG. 9.

A range of w=100 pixels surrounding the core in the derivative array $G_h(x)$, see FIG. 9, is then selected in a block 89. The values of the derivative array are then compared to corresponding derivative arrays $S_n(x)$ for known fibers. Before the comparison the derivative array or arrays can be normalized and/or displaced so that the comparison can be made in an appropriate way. In the comparison the mean-square error $E_n$ of the derivative array $G_h(x)$ considered as a deviation of the array $S_n(x)$ of each of the known fiber types is calculated according to $$E_n = \sum_{x=1}^{100} [S_n(x) - G(x)]^2 \qquad (4)$$

Thereafter the minimum value $E_m$ of the calculated errors is determined in a block 91, m thus defining the fiber type most resembling the tested fiber. This minimum value is in a next block 93 compared to a threshold value $\epsilon_1$. If the minimum value $E_m$ is not below this threshold, the fiber is considered to be an unknown type and a signal thereof to some control device in order to e.g. showing some message on a display is sent in a block 95. If the minimum value is below the threshold, also the intensity profile obtained from the cold image will be evaluated.

Thus, in a block 97 the cold intensity profile $F_c(x)$ is low-pass filtered by subjecting it to a 3×1 median filter. Thereupon, in the block 99 the filtered intensity profile is normalized and displaced to some predetermined x-position and in the corresponding way, as previously executed in the block 89, the mean-square error $E_c$ is calculated for the filtered and normalized intensity profile as compared to the cold image intensity profile $Q_m$ of the m:th fiber type. The calculated mean-square error $E_c$ is in a block 101 compared to a threshold value $\epsilon_2$. If the result of the comparison is that the mean-square error is smaller than the threshold value, the tested fiber is determined to be type m and a signal thereof is sent in a block 103 to some control device for e.g. appropriately setting welding parameters and/or displaying some message. If it is determined in the block 101 that the mean-square error is not smaller than the second threshold value the tested fiber is decided not to be any of the known types and then a signal thereof is sent in a block 105 to some control device.

Figure 12A:
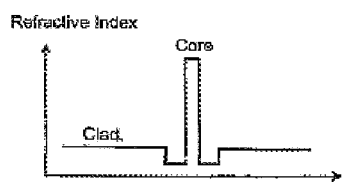
FIG. 12a is a diagram of the refractive index profile of a region at the core of a depressed cladding, highly doped dispersion shifted fiber.
Figure 12C:
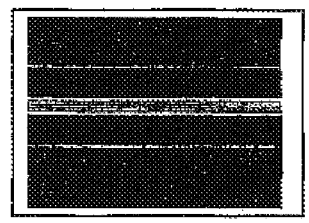
FIG. 12b is a diagram showing measured pixel grey scale values $Q_m(x)$ and $S_h(x)$ for cold and hot fibers respectively and the derivative array $G_h(X)$ of the hot profile of the fiber of FIG. 12a, FIGS. 12c, 12d are cold and hot images of the fiber of FIG. 12a, FIGS. 13a, 13b, 13c, and 13d are diagrams and pictures corresponding to those in FIGS. 12a, 12b, 12c, and 12d but for a matched cladding, erbium doped fiber.
Figure 12B:
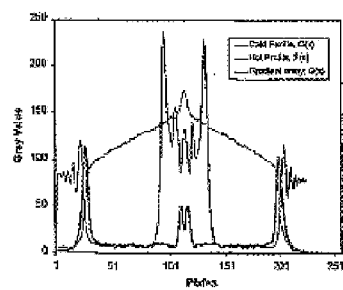
Figure 12D:
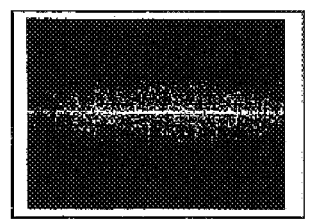
Figure 13A:
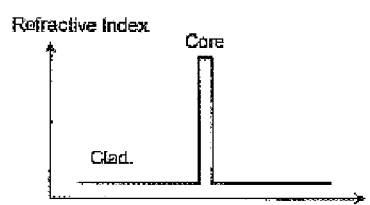
Figure 13C:
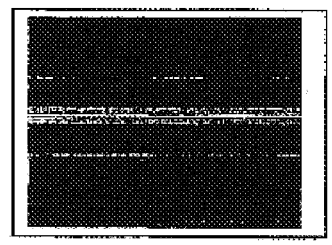
Figure 13B:
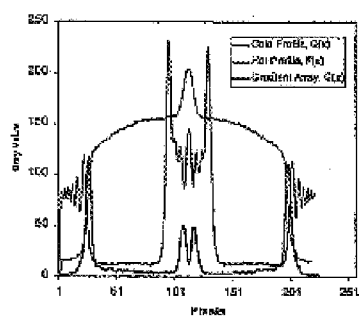
Figure 13D:
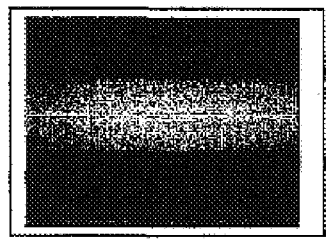
Figure 14A:
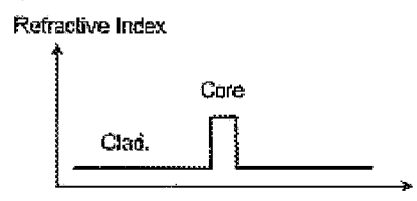
FIGS. 14a, 14b, 14c, and 14d are diagrams and pictures corresponding to those in FIGS. 12a, 12b, 12c, and 12d but for a standard single mode fiber, SMF 28.
Figure 14C:
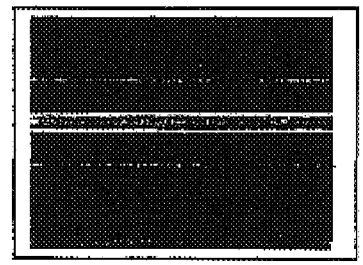
Figure 14B:
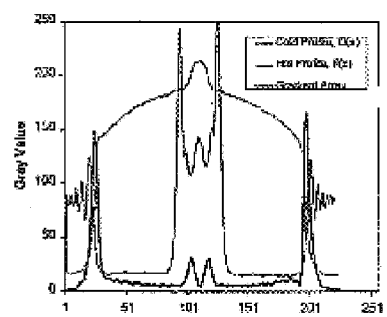
Figure 14D:
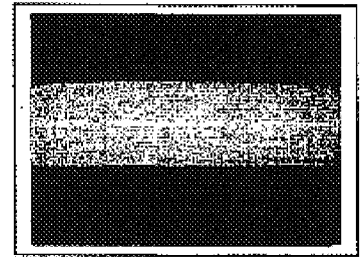
Figure 15A:
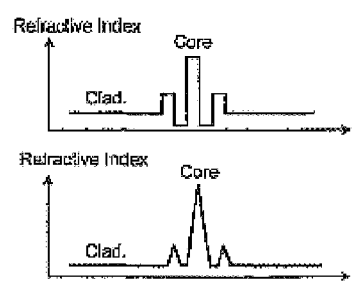
FIGS. 15a, 15b, 15c, and 15d are diagrams and pictures corresponding to those in FIGS. 12a, 12b, 12c, and 12d but for a large effective area none zero dispersion shifted fiber.
Figure 15C:
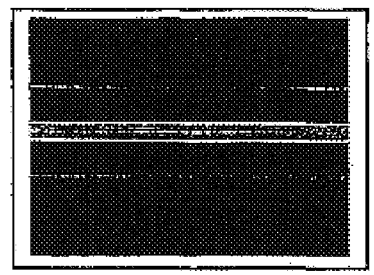
Figure 15B:
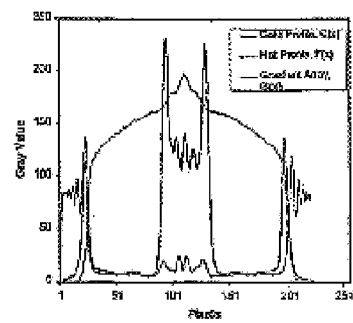
Figure 15D:
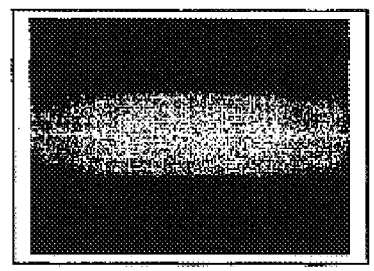
Figure 16A:
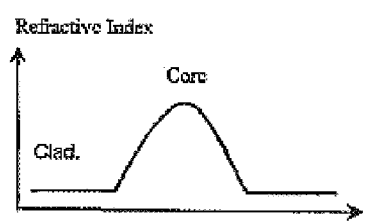
FIGS. 16a, 16b, 16c, and 16d are diagrams and pictures corresponding to those in FIGS. 12a, 12b, 12c, and 12d but for a multi mode fiber.
Figure 16C:
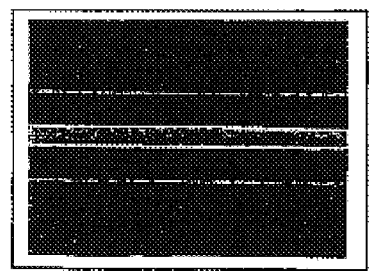
Figure 16B:
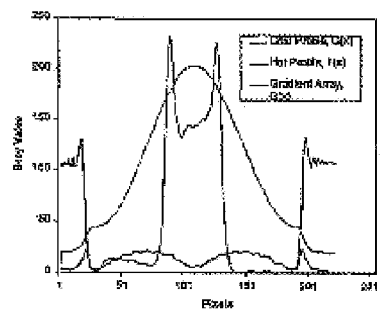
Figure 16D:
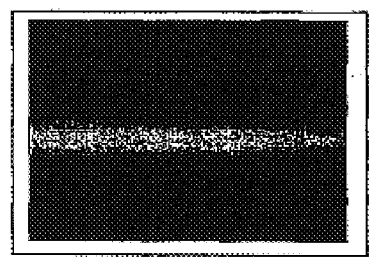
Figure 17A:
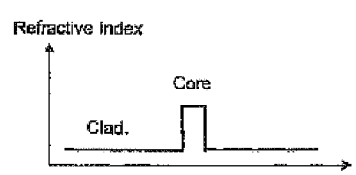
FIGS. 17a, 17b, 17c, and 17d are diagrams and pictures corresponding to those in FIGS. 12a, 12b, 12c, and 12d but for a pure silica core single mode fiber.
Figure 17C:
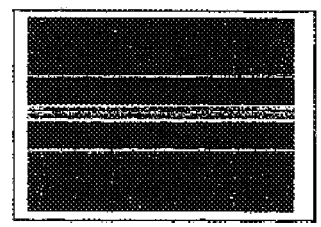
Figure 17B:
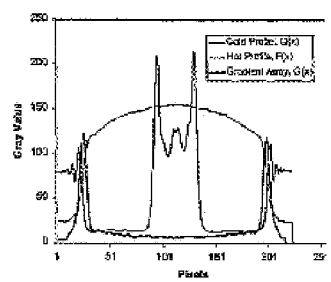
Figure 17D:
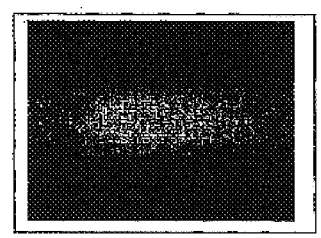

FIG. 12a is a diagram of the refractive index profile of the core, FIG. 12b is a diagram showing measured pixel gray level values $Q_m(x)$ and $S_n(x)$ for cold and hot fibers respectively and the derivative array $G_h(X)$ of the hot profile and FIGS. 12c–12d show hot and cold images of a depressed cladding, highly doped dispersion shifted fiber. FIGS. 13a–13d are the corresponding diagrams and pictures for an erbium doped fiber, FIGS. 14a–14d for a standard single-mode fiber, SMF-28, FIGS. 15a–15d a for large effective area none-zero dispersion shifted fiber, FIGS. 16a–16d for a multi-mode fiber, and FIGS. 17a–17d for a pure silica core single-mode fiber.

While specific embodiments of the invention have been illustrated and described herein, it is realized that numerous additional advantages, modifications and changes will readily occur to those skilled in the art. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents. It is therefore to be understood that the appended claims are intended to cover all such modifications and changes as fall within a true spirit and scope of the invention.

What is claimed is:

1. A method of determining the type of an optical fiber, the method comprising the steps of:
   heating a region of the optical fiber to such a temperature that an observable amount of light is emitted,
   recording the light emitted during the heating as a first picture,
   determining from the first picture a first light intensity profile comprising values of the intensity of light emitted from all points in a line substantially perpendicular to the longitudinal direction of the fiber, as viewed in an observation direction, as a function of position along the line, and
   analyzing the determined first light intensity profile by calculating the derivative of the determined first light intensity profile and comparing the calculated derivative to the derivative of first light intensity profiles previously determined for a plurality of optical fibers of known different types.

2. The method claim 1, wherein in the step of determining the first light intensity profile, a local mean is calculated for each point in the first picture to produce a smoothed picture.

3. The method of claim 1, wherein in the step of analyzing, the determined first light intensity profile is low-pass filtered before calculating the derivative.

4. The method claim 1, wherein in the step of analyzing, the derivative of only a central portion of the determined first light intensity profile is calculated and compared to the derivative of corresponding central portions of the first light intensity profiles previously determined for the plurality of optical fibers of known different types.

5. The method of claim 1, comprising the further steps of:
   taking a second picture of a region of the optical fiber in an unheated state using a high-resolving optical system to produce in the picture an image of the core of the optical fiber,
   determining from the second picture a second light intensity profile comprising values of the intensity of light emitted from all points in a line substantially perpendicular to the longitudinal direction of the fiber, as viewed in an observation direction, as a function of the position along the line,
   comparing the determined second light intensity profile to second light intensity profiles previously determined for the plurality of optical fibers of known different types, and
   evaluating the results of the comparing of the first and second light intensity profiles to find the type of known optical fiber which most resembles the optical fiber for which the pictures have been taken.

6. The method claim 5, wherein in the step of determining a second light intensity profile, directly after the determining, a local mean is calculated for each point in the determined second light intensity profile to produce a smoothed second light intensity profile which is then compared.

7. The method of claim 5, wherein in the step of determining a second light intensity profile, directly after the determining, the determined second light intensity profile is low-pass filtered before comparing.

8. A method of splicing two optical fibers to each other, comprising the steps of:
   determining the type of each of the two optical fibers by:
      heating a region of said optical fiber to such a temperature that an observable amount of light is emitted,
      recording the light emitted during the heating as a first picture,
      determining from the first picture a first light intensity profile comprising values of the intensity of light emitted from all points in a line substantially perpendicular to the longitudinal direction of the fiber, as viewed in an observation direction as a function of position along the line, and
      analyzing the determined light intensity profile by calculating the derivative of the determined first light intensity profile and comparing the calculated derivative to the derivative of first light intensity profiles previously determined for a plurality of optical fibers of known different types in order to obtain, from a result of the comparing the type of said optical fiber,
   aligning one end of a first one of the two optical fibers with one end of a second one of the optical fibers,
   moving said end of the first optical fiber to place the end surface of said end at the end surface of the end of the second optical fiber,
   heating a region of said ends of the two optical fibers at said end surfaces to make them be fused to each other, and
   allowing the region to cool,
   wherein in the step of moving or in the step of heating at least one physical parameter used in said steps is determined from the obtained types of the first and second optical fibers.

9. The method of claim 8 in the heating step, an electric arc generated between electrodes is used, and in setting said at least one physical parameter, the intensity of electrical current flowing between electrodes is set.

10. The method of claim 8, wherein in setting at least one physical parameter, at least one of the following is made:
    setting the duration of heating of the region,
    setting the intensity of heating of the region, and
    setting in the step of moving an overlap distance.

11. A device for determining the type of an optical fiber, the device comprising:
    a heating device for heating a region of the optical fiber to such a temperature that an observable amount of light is emitted,
    an optical system for imaging the region of the optical fiber as a first picture,
    a light sensitive device for recording light emitted when heating the region,
    a determining device connected to the light sensitive device for determining from the first picture a first light intensity profile comprising values of the intensity of light emitted from all points in a line substantially perpendicular to the longitudinal direction of the fiber, as viewed in an observation direction, as a function of position along the line, and an analyzer connected to the determining device for analyzing the determined first light intensity profile comprising:

a calculator unit for calculating the derivative of the determined first light intensity profile, a comparator connected to the calculator for comparing derivatives of light intensity profiles previously determined for a plurality of optical fibers of known different types to the calculated derivative of the first light intensity profile, and a decision unit, connected to the comparator, for deciding that the optical fiber is the same type as one of the known types of optical fibers having a closest derivative of the light intensity profile to the calculated derivative.

12. The device of claim 11, wherein the comparator is arranged to calculate values representing the differences between the derivatives of the light intensity profiles for the plurality of optical fibers of known different types and the calculated derivative of the first light intensity profile, and the decision unit is arranged to compare the calculated value representing the differences between the derivative of the light intensity profile for said one of the optical fibers of known different types and the calculated derivative of the first light intensity profile to a threshold value and only deciding the optical fiber to be same type as said one of the optical fibers in the case where the said value is not greater than the threshold value.

13. The device of claim 11, wherein the optical system is high resolving allowing, for a correctly setting, imaging the region of the optical fiber in an unheated state to produce in a produced second picture an image of the core of the optical fiber, the light sensitive device recording also the second picture, the determining device is arranged to determine from the second picture a second light intensity profile comprising values of the intensity of light emitted from all points in a line substantially perpendicular to the longitudinal direction of the fiber, as viewed in an observation direction, as a function of position along the line, the comparator is arranged to compare the determined second light intensity profile to second light intensity profiles previously determined for the plurality of optical fibers of known different types, and the decision unit is arranged to evaluate the results of the comparing of the derivatives of the first light intensity profiles and the second light intensity profiles to find the type of known optical fiber which most resembles the optical fiber for which the first and second pictures have been recorded.

14. A splicer for splicing two optical fibers to each other, comprising:

a device for determining the type of an optical fiber the device including:

a heating device for heating a region of the optical fiber to such a temperature that an observable amount of light is emitted, an optical system for imaging the region of the optical fiber as a first picture, a light sensitive device for recording light emitted when heating the region, a determining device connected to the light sensitive device for determining from the first picture a first light intensity profile comprising values of the intensity of light emitted from all points in a line substantially perpendicular to the longitudinal direction of the fiber, as viewed in an observation direction, as a function of position along the line, and an analyzer connected to the determining device for analyzing the determined light intensity profile comprising:

a calculating unit for calculating the derivative of the determined first light intensity profile, a comparator connected to the calculating unit for comparing derivatives of light intensity profiles previously determined for a plurality of optical fibers of known different types to the calculated derivative of the first light intensity profile, and a decision unit connected to the comparator for deciding that the optical fiber is the same type as one of the known types of optical fibers having a closest derivative of the light intensity profile to the calculated derivative, the splicer further comprising:

an aligning device for aligning one end of a first one of the optical fibers with one end of a second one of the optical fibers, a moving device for moving the end of the first optical fiber to place the end surface of this end at the end surface of the end of the second optical fiber, and a heating device for heating a region of the ends of the optical fibers at the end surfaces to make them be fused to each other, and a controller connected to the device for determining the type of an optical fiber and arranged to command the device to determine the types of the optical fibers to be spliced before making the splice, to then find a value of at least one of physical parameters adapted to the determined types and control the respective one of the aligning, moving and heating device to use the found value.

* * * * *